United States Patent
Fukuda

(10) Patent No.: US 8,679,144 B2
(45) Date of Patent: Mar. 25, 2014

(54) PUNCTURE NEEDLE CARTRIDGE AND PUNCTURE DEVICE

(75) Inventor: Mitsuo Fukuda, Nishinomiya (JP)

(73) Assignee: Lightnix, Inc., Hyogo (JP)

( * ) Notice: Subject to any disclaimer, the term of this patent is extended or adjusted under 35 U.S.C. 154(b) by 189 days.

(21) Appl. No.: 12/737,041

(22) PCT Filed: Jun. 4, 2009

(86) PCT No.: PCT/JP2009/060284
§ 371 (c)(1),
(2), (4) Date: Dec. 3, 2010

(87) PCT Pub. No.: WO2009/148133
PCT Pub. Date: Dec. 10, 2009

(65) Prior Publication Data
US 2012/0089050 A1    Apr. 12, 2012

(30) Foreign Application Priority Data
Jun. 5, 2008   (JP) ................................ 2008-147629

(51) Int. Cl.
*A61B 5/151*   (2006.01)

(52) U.S. Cl.
USPC ........................... 606/181; 600/583; 606/185

(58) Field of Classification Search
USPC .................. 600/583, 573; 606/181, 182, 186
See application file for complete search history.

(56) References Cited

U.S. PATENT DOCUMENTS

| | | | |
|---|---|---|---|
| 4,535,769 A * | 8/1985 | Burns | 606/182 |
| 4,990,154 A | 2/1991 | Brown et al. | |
| 6,887,254 B1 * | 5/2005 | Curie | 606/181 |
| 7,842,059 B2 * | 11/2010 | Rutynowski | 606/181 |
| 7,955,347 B2 * | 6/2011 | Stout | 606/181 |

(Continued)

FOREIGN PATENT DOCUMENTS

| | | |
|---|---|---|
| DE | 10 2005 003789 A1 | 7/2006 |
| EP | 0403873 A1 | 12/1990 |
| EP | 1491143 A1 | 12/2004 |
| EP | 1716808 A1 | 11/2006 |

(Continued)

OTHER PUBLICATIONS

International Search Report dated Jul. 21, 2009, issued for PCT/JP2009/060284.

(Continued)

*Primary Examiner* — Max Hindenburg
*Assistant Examiner* — John Pani
(74) *Attorney, Agent, or Firm* — Harness, Dickey & Pierce, P.L.C.

(57) ABSTRACT

A puncture needle cartridge 20 detachably mounted on a puncturing device body to form a puncturing device is provided with a needle body 21 having a puncturing portion 212a, and also with a casing 22 for housing the needle body 21 and having openings 223, 224 that are respectively formed in front of and behind the needle body 21. The needle body 21 is mounted so as to be movable between a retracted position, wherein the tip 212c of the puncturing portion is retraced in the casing 22, and an extended position, wherein the tip 212c of the puncturing portion is projected outward from the casing 22 by receiving a pressing force from the puncturing device body. The needle body 21 has a biasing means for biasing the needle body 21 from an extended position towards a retracted position. The puncture needle cartridge can be mass-produced at low cost, and enables a user to perform puncturing safely and easily.

15 Claims, 15 Drawing Sheets

(56) References Cited

U.S. PATENT DOCUMENTS

| | | |
|---|---|---|
| 8,109,960 B2 * | 2/2012 | Sarna et al. .................. 606/182 |
| 2004/0059366 A1 | 3/2004 | Sato et al. |
| 2004/0158271 A1 | 8/2004 | Hamamoto |
| 2006/0052809 A1 | 3/2006 | Karbowniczek et al. |
| 2006/0129173 A1 | 6/2006 | Wilkinson |
| 2007/0016239 A1 | 1/2007 | Sato et al. |
| 2007/0162065 A1 * | 7/2007 | Li et al. .......................... 606/182 |
| 2007/0185515 A1 * | 8/2007 | Stout ............................ 606/181 |
| 2008/0097244 A1 | 4/2008 | Arnitz |
| 2008/0188882 A1 | 8/2008 | Dicesare et al. |
| 2009/0036915 A1 | 2/2009 | Karbowniczek et al. |
| 2009/0093832 A1 | 4/2009 | Fukuzawa |
| 2009/0198265 A1 | 8/2009 | Ono et al. |
| 2010/0198246 A1 | 8/2010 | Ono et al. |
| 2010/0234868 A1 | 9/2010 | Ono et al. |

FOREIGN PATENT DOCUMENTS

| | | |
|---|---|---|
| JP | 06-38910 U | 5/1994 |
| JP | 2006-314718 A | 11/2006 |
| JP | 2007-536008 A | 12/2007 |
| JP | 2007-536013 A | 12/2007 |
| WO | WO 9219164 A1 * | 11/1992 |
| WO | WO-02/054953 A1 | 7/2002 |
| WO | WO-02/100272 A1 | 12/2002 |
| WO | WO 2007050528 A1 * | 5/2007 |
| WO | WO-2007/088875 A1 | 8/2007 |
| WO | WO-2007/105617 A1 | 9/2007 |

OTHER PUBLICATIONS

European Search Report dated Jul. 27, 2011 issued in European Application No. 09758400.7.

* cited by examiner (a)

(b)

(a)

(b)

(a)

(b)

PUNCTURE NEEDLE CARTRIDGE AND PUNCTURE DEVICE

TECHNICAL FIELD

The present invention relates to a puncture needle cartridge that is mounted on a puncturing device body to perform puncturing, and a puncturing device.

BACKGROUND ART

Puncturing devices are provided with a puncture needle for puncturing tissue, such as that of a fingertip. Puncturing devices are used, for example, to collect a small amount of blood during blood glucose measurement. To prevent infection, puncture needles must be replaced after use. Therefore, puncturing devices configured to enable replacement of puncture needles have hitherto been known.

For example, Patent Literature 1 (PTL 1) discloses a puncture instrument comprising a puncture needle holding portion formed at the front end of a plunger; and a puncture needle cartridge that is detachably fitted to the puncture needle holding portion. The puncture needle cartridge is such that a body portion having a puncture needle attached thereto is slidably mounted within a cover, and the body portion is moved by the action of a plunger so as to perform puncturing.

CITATION LIST

Patent Literature

PTL 1: Japanese Unexamined Patent Publication No. 2006-314718

SUMMARY OF INVENTION

Technical Problem

However, because puncture needles of known puncture needle cartridges may accidentally project from the cover, the puncture needles must be protected with caps or the like before use. Further, puncturing devices must be provided with a mechanism for re-capping and returning the puncture needle into the cover for disposal after use. Accordingly, for known puncture needle cartridges, there is room for improvement in terms of workability and cost.

Thus, an object of the present invention is to provide a puncturing device, and a puncture needle cartridge that can be mass-produced at low cost; and that enables a user to perform puncturing safely and easily.

Solution to Problem

The object of the present invention can be achieved by a puncture needle cartridge for detachably mounting on a puncturing device body so as to form a puncturing device. The puncture needle cartridge comprises a needle body comprising a puncturing portion, and a casing for housing the needle body. The casing has openings that are respectively formed in front of and behind the needle body. The needle body is mounted so as to be movable between a retracted position, wherein the tip of the puncturing portion is retracted in the casing, and an extended position, wherein the tip of the puncturing portion projects outward from the casing by receiving a pressing force from the puncturing device body. The needle body comprises a biasing means for biasing the needle body from an extended position towards a retracted position.

In this puncture needle cartridge, the biasing means preferably comprises a pair of elastic bodies that are respectively disposed on laterally opposite sides of the needle body.

The biasing means preferably comprises an elastically deformable flexible member, a first end of which is fixed to the inner surface of the casing, and a second end of which is engaged with the needle body. In the above structure, the engaging portion of the needle body to be engaged with the second end of the flexible member preferably comprises a tapered inclined surface. Further, the front end of the inclined surface preferably has a step that can be brought into contact with the front surface of the flexible member.

The second end of the flexible member to be engaged with the needle body preferably has a circular arc shape in plan view.

The needle body and the casing are preferably formed integrally using a biocompatible material.

The above object of the present invention can be achieved by a puncturing device comprising a needle body having a puncturing portion, and a casing for housing the needle body, the casing having openings respectively formed in front of and behind the needle body. The needle body is configured to be pressed through the rear opening of the casing, and mounted so as to be movable between a retracted position, wherein the tip of the puncturing portion is retracted in the casing; and an extended position, wherein the tip of the puncturing portion is projected outward from the casing by a pressing force. The needle body is provided with a biasing means for biasing the needle body from an extended position towards a retracted position.

Advantageous Effects of Invention

The puncture needle cartridge and the puncturing device of the present invention can be mass-produced at low cost, and enables a user to perform puncturing safely and easily.

BRIEF DESCRIPTION OF DRAWINGS

FIG. 7(a) shows a state before puncturing, and FIG. 7(b) shows a state during puncturing.

FIG. 13(a) shows a state before puncturing, and FIG. 13(b) shows a state during puncturing.

FIG. 16(a) is a view from above, and FIG. 16(b) is a view from below.

DESCRIPTION OF EMBODIMENTS

Figure 1:
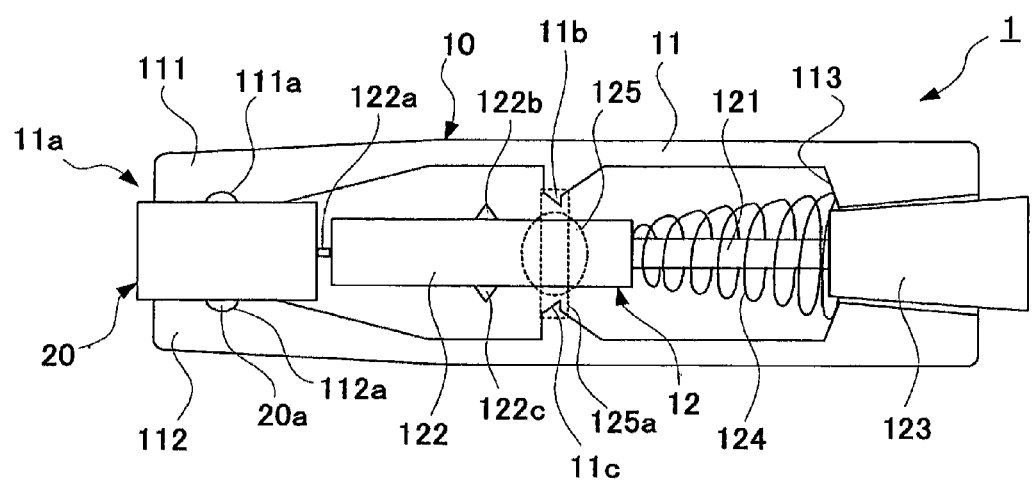
FIG. 1 is a cross-sectional view of a puncturing device comprising a puncture needle cartridge according to one embodiment of the present invention.

Embodiments of the present invention will be described with reference to the accompanying drawings. FIG. 1 is a cross-sectional view of a puncturing device comprising a puncture needle cartridge according to one embodiment of the present invention. As shown in FIG. 1, the puncturing device 1 comprises a puncturing device body 10, and a puncture needle cartridge 20 detachably mounted on the puncturing device body 10. In the following drawings, the same reference numerals are assigned to the same elements, and detailed descriptions thereof will be omitted.

The puncturing device body 10 comprises a housing 11, and a plunger 12 accommodated in the housing 11. The front side of the housing 11 has a mounting portion 11a to which the puncture needle cartridge 20 is mounted. FIG. 1 is a cross-sectional view with the upper lid of the housing removed.

The rear side of the mounting portion 11a is integrally formed with the housing 11, and the front side of the mounting portion 11 comprises a pair of flexible holding elements 111, 112. The puncture needle cartridge 20 is inserted between the holding elements 111, 112 from the front side to expand the space between the holding elements 111, 112, allowing the ribs 20a formed on the outer surface of the puncture needle cartridge 20 to engage with engagement grooves 111a, 112a of the holding elements 111, 112, and allowing the puncture needle cartridge 20 to be held by the elastic force of the holding elements 111, 112. Respective attachment and detachment of the puncture needle cartridge 20 to and from the puncturing device body 10 can be accomplished from the front side, as shown in this embodiment. Alternatively, the attachment and detachment can be done from above or below (i.e., from a direction perpendicular to the plane of FIG. 1).

The plunger 12 comprises a straight rod 121, a pushing member 122 disposed on a front end thereof, and a drawer 123 disposed on a rear end thereof. The plunger 12 is biased in a forward direction by a coil spring externally fitted between the pushing member 122 and the inner surface of the rear end of the housing 11. The drawer 123 projects rearwardly of the housing 11, and the plunger 12 can be moved backward by holding and pulling this projection.

The pushing member 122 comprises a driving projection 122a disposed on a front end thereof, and engaging projections 122b, 122c disposed on laterally opposite sides thereof. When the plunger 12 moves forward, the driving projection 122a exerts a pressing force on the puncture needle cartridge 20. When the plunger 12 moves backward, the engaging projections 122b, 122c are engaged with holding portions 11b, 11c that project from the inner circumferential surface of the housing 11.

The upper lid (not shown) of the housing 11 has a puncture button 125 comprising a flexible member. A belt-like release member 125a, both ends of which are bent downward, is provided below the puncture button 125. When the puncture button 125 is pressed with a finger or the like, both ends of the release member 125a push the holding portions 11b, 11c downward due to the deflection of the button, so as to disengage the holding portions 11b, 11d from the engaging projections 122b, 122c. When the finger is removed from the puncture button 125, the puncture button 125 and the release member 125a return to their original positions. Because FIG. 1 is a cross-sectional view with the upper lid of the housing 11 removed, the puncture button 125 and the release member 125a are indicated by dashed lines.

Figure 2:
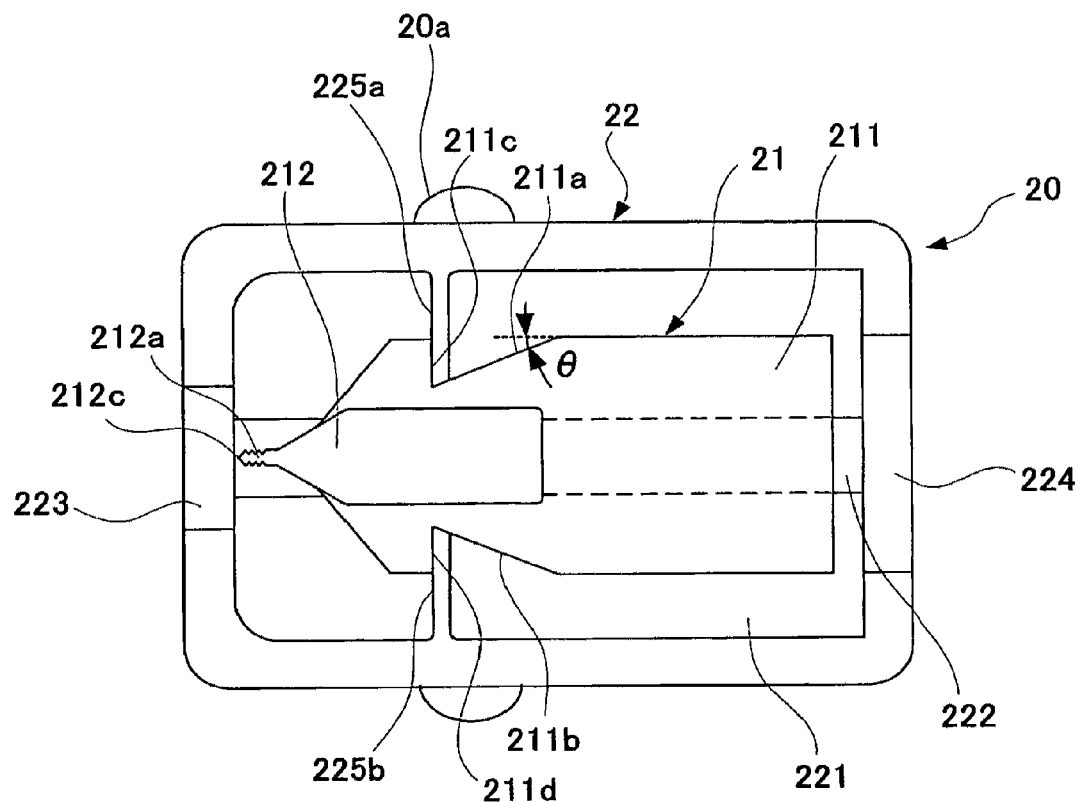
FIG. 2 is a cross-sectional view of the puncture needle cartridge.

FIG. 2 is an enlarged cross-sectional view of the puncture needle cartridge 20 shown in FIG. 1. As shown in FIG. 2, the puncture needle cartridge 20 comprises a needle body 21, and a cabinet-like casing 22 for housing the needle body 21. FIG. 2 is a view with the upper lid of the casing removed.

Figure 3:
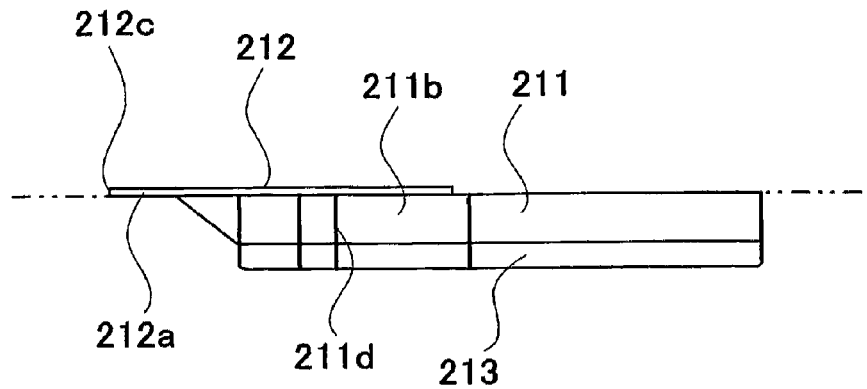
FIG. 3 is a side view of the needle body.

The needle body 21 comprises a pedestal portion 211, and a support 221 provided in the upper portion on the front side of the pedestal portion 211. As shown in the side view of FIG. 3, the needle body 21 has a guide projection 213 that projects downwardly from the center of the lower portion of the pedestal portion 211. The guide projection 213 is engaged with a guide groove 222 that is formed on the bottom surface 221 of the casing 22 so as to extend in the front-rear direction. The needle body 21 is mounted so as to be movable forward and backward along the guide groove 22 while sliding in contact with the upper and lower inner surfaces of the casing 22.

The pedestal portion 211 has a pair of engaging portions 211a, 211b that are respectively formed on the right and left sides with respect to the axis of the support portion 212 interposed therebetween. Each engaging portion has an inclined surface that tapers forward. In this embodiment, the engaging portions 211a, 211b are formed by partially notching respective central portions on right and left sides of the pedestal portion 211, allowing the front ends of the engaging portions 211a, 211b to have steps 211c, 211d.

Figure 4:
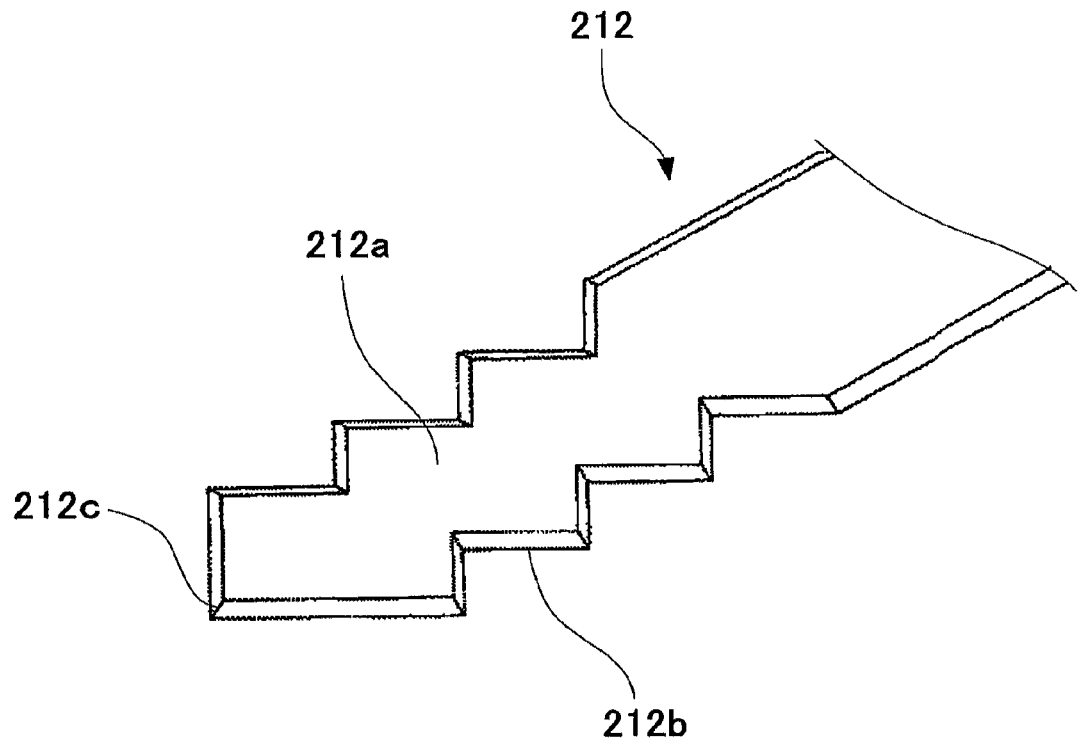
FIG. 4 is a perspective view of the puncturing portion.
Figure 5:
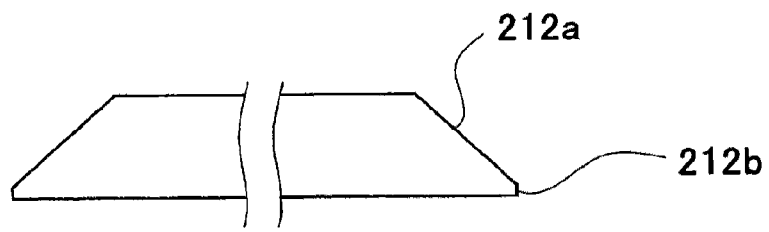
FIG. 5 is a cross-sectional view of the puncturing portion.

As shown in FIG. 4, the puncturing portion 212a of the support portion 212 is formed in such a manner that its cross-sectional area alternately repeats monotonic increase and monotonic decrease to reduce pain during puncture. As shown in FIG. 5, the cross section perpendicular to the axis of puncturing portion 212a has a generally trapezoidal shape, and an upstanding portion 212b of a constant width is formed on the base of the trapezoid. Strictly speaking, the cross section is hexagonal. The upstanding portion 212b has the following advantage. When the needle body 21 is formed by injection molding and/or extrusion molding in such a manner that the mating surface between the upper mold and the lower mold becomes an interface (indicated by long dashed double-short dashed lines in FIG. 3) between the pedestal portion 211 and the support portion 212, an injection material can flow through the upstanding portion 212b and easily spread over the support portion 212, thus sharpening the tip 211c. However, the shape of the cross section of the puncturing portion 212a does not have to be generally trapezoidal, and may be, for example, triangular or another polygonal shape. Insofar as the tip is sharp enough to enable puncturing, the cross-sectional shape is not particularly limited.

The support portion 212 is preferably formed using a biocompatible material. Preferable examples of such biocompatible materials include, but are not limited to, polylactic acid, polyglycolic acid, and like biodegradable polymers (including, for example, biodegradable copolymers). Other examples thereof include polyvinyl chloride, polyethylene glycol, and like high molecular weight polymers; cellulose, starch, and like biopolymers; collagen, gelatin, and like proteins; and ceramic, carbon, and like biocompatible inorganic materials. Further, biocompatible metal materials, such as stainless steel, cobalt, and titanium materials, can also be used to form the support portion 212. When the pedestal portion 211 is integrally molded with the support portion 212, as shown in this embodiment, the same material as for the support portion 212 is used for the pedestal portion 211. However, different materials may be used to form the pedestal portion 211 and the support portion 212.

Figure 6:
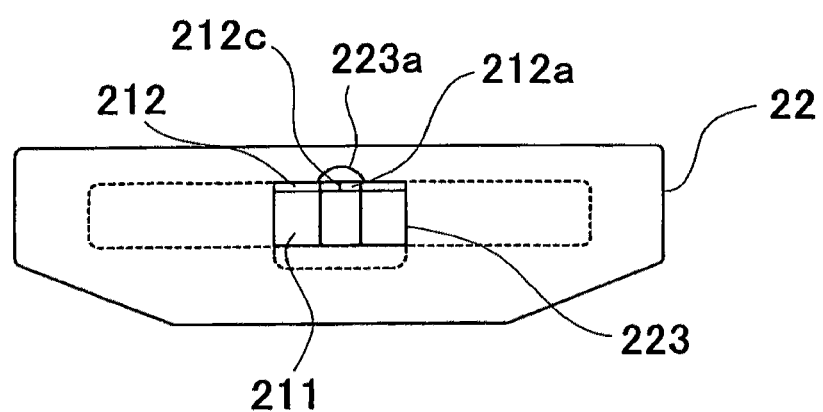
FIG. 6 is a front elevation view of the puncture needle cartridge.

The casing 22 has openings 223, 224 at positions facing the front and rear sides of the needle body 21. When the plunger 12 of the puncturing device body 10 shown in FIG. 1 moves forward, the driving projection 122a of the pushing member 122 pushes the rear end surface of the pedestal portion 211, allowing the tip 212c of the support portion 212 to project from the opening 223. As shown in FIG. 6, the anterior opening 223 has a notch 223a on the upper edge thereof so as to keep the tip 212c intact during the respective extension and retraction of the puncturing portion 212a of the support portion 212 away from and towards the casing.

A pair of flexible members 225a, 225b project from the inner wall surface of the casing 22 in opposite directions to face each other. These flexible members 225a, 225b are elastic bodies that are integrally molded with the casing 22. As shown in FIG. 1, the length of the projection is adjusted to allow the front end of the flexible members 225a, 225b in the extension direction to abut on the narrowest part of the engaging portion 211a, 211b. According to this embodiment, the flexible members 225a, 225b have a belt-like (planar) shape. However, the shape of the flexible members is not particularly limited, insofar as the flexible members can be deflected by elastic deformation. The flexible members may be formed into other shapes, such as a curved or linear shape.

The casing 22 is preferably formed using an elastic material. For example, the same material as that for the pedestal portion 211 and the support portion 212 may be used to form the casing 22. The needle body 21 and the casing 22, which are components of the puncture needle cartridge 20, can be formed using biocompatible materials as described above. Examples of such biocompatible materials include high molecular weight polymers, biopolymers, proteins, and biocompatible inorganic materials.

As high molecular weight polymers, those suitable for medical use are preferably used. Examples of such polymers include polyvinyl chloride, polyethylene glycol, parylene, polyethylene, polypropylene, silicone, polyisoprene, polymethylmethacrylate, fluororesins, polyether imide, polyethylene oxide, polyethylene terephthalate, polyethylene succinate, polybutylene terephthalate, polybutylene succinate, polybutylene succinate carbonate, polyphenylene oxide, polyphenylene sulfide, polyformaldehyde, polyanhydride, polyamide (6 nylon) 66 nylon, polybutadiene, polyvinyl acetate, polyvinyl alcohol, polyvinylpyrrolidone, polyesteramide, polymethyl methacrylate, polyacrylonitrile, polysulfone, polyether sulphone, ABS resins, polycarbonate, polyurethanes (polyetherurethane, polyesterurethane, polyether urethane urea), polyvinylidene chloride, polystyrene, polyacetal, polybutadiene, ethylene vinyl acetate copolymers, ethylene vinyl alcohol copolymers, ethylene propylene copolymers, polyhydroxyethylmethacrylate, polyhydrobutyrate, polyorthoester, polylactic acid, polyglycol, polycaprolactone, polylactic acid copolymers, polyglycolic acid-glycol copolymers, polycapronolactone copolymers, polydioxanone, perfluoroethylene-propylene copolymers, cyanoacrylate polymers, polybutylcyanoacrylate, polyallyl ether ketone, epoxy resins, polyester resins, polyimide, phenolic resins, acrylic resins, and the like.

Examples of the biopolymer include cellulose, starch, chitin chitosan, agar, carrageenan, alginic acid, agarose, pullulan, mannan, curdlan, xanthane gum, gellan gum, pectin, xyloglucan, guar gum, lignin, oligosaccharide, hyaluronic acid, schizophyllan, lentinan, and the like. Examples of the protein include collagen, gelatin, keratin, fibroin, glue, sericin, vegetable proteins, milk protein, egg protein, synthetic proteins, heparin, nucleic acid and the like, as well as sugar, candies, glucose, maltose, sucrose, and polymer alloys thereof.

Examples of the biocompatible inorganic material include ceramics such as glass, nanocomposite ceramics, $Al_2O_3/ZrO_2$ composite ceramics, $Si_3N_4$ nano-composite materials, hydroxyapatite, calcium carbonate, carbon, graphite (nanografiber), carbon nanotube (CNT), fullerene composite materials, hydroxyapatite polymer composite materials, cobalt-chromium alloys, stainless steel, titanium, titanium alloys, and the like.

Among such biocompatible materials, biodegradable materials, such as polylactic acid, polyglycolic acid, polycaprolactone, collagen, starch, hyaluronic acid, alginic acid, chitin, chitosan, cellulose, gelatin, and like biodegradable polymers, and compounds thereof, are preferable for use, because such materials decompose in the presence of microorganisms and thus can be easily discarded after use.

Next, the operation of the puncturing device 1 will be described. First, as shown in FIG. 1, the puncture needle cartridge 20 is mounted on the mounting portion 11a of puncturing device body 10. As shown in FIG. 2, the steps 211c, 211d are in contact with the front surface of flexible members 225a, 225b while the tips of the flexible members 225a and 225b are abutting on the surface of engaging portions 211a, 211b, whereby the needle body 21 of the puncture needle cartridge 20 is locked. The needle body 21 in this initial state is thus held in a retracted position, wherein the tip 212c of the puncturing portion 212a is retracted in the casing 22.

Figure 7:
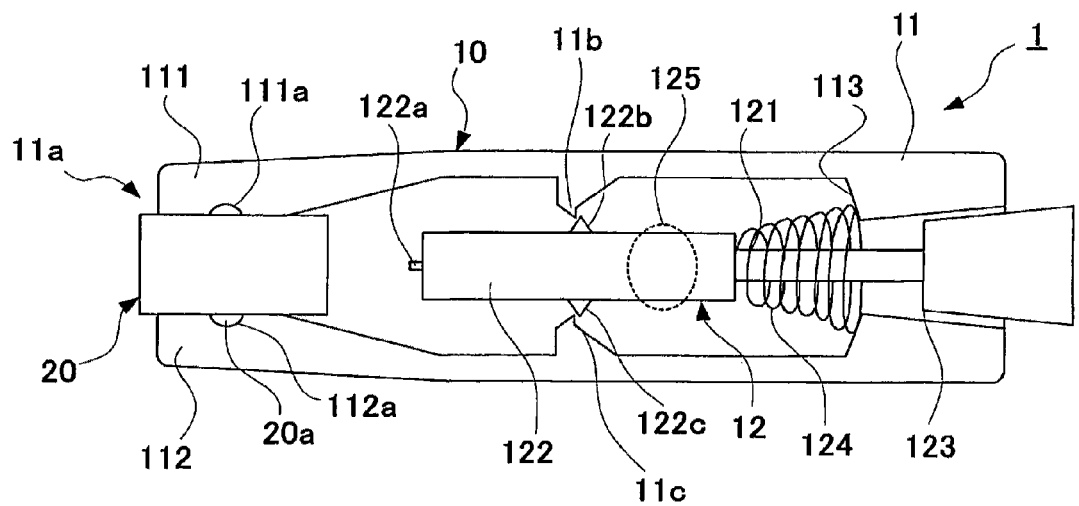
FIG. 7 shows cross-sectional views of the puncturing device.
Figure 7:
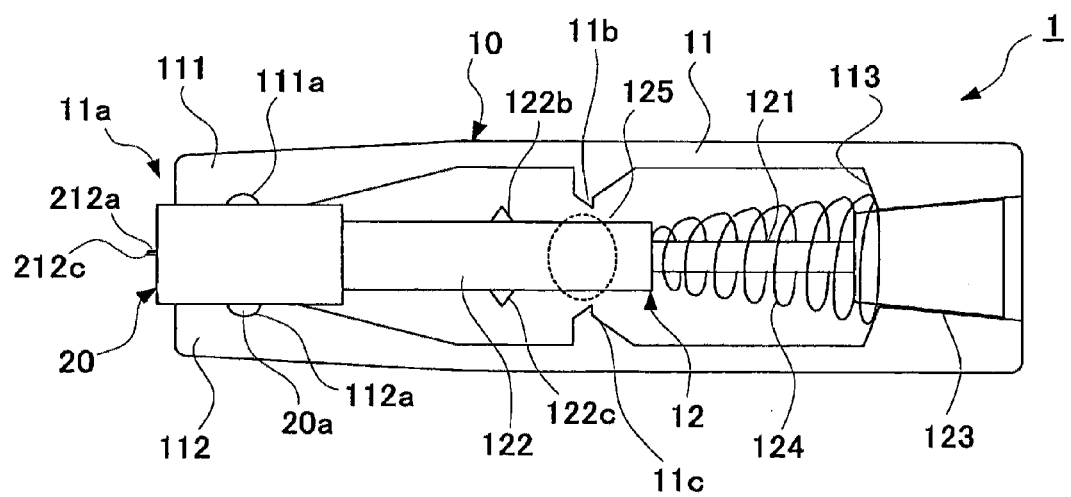

When the drawer 123 is held and pulled rearward as shown in FIG. 7(a), the pushing member 122 is moved backward against the biasing force of the coil spring 124, allowing the engaging projections 122b, 122c of the pushing member 122 to ride over the holding portions 11b, 11c and become locked thereby. Then, when a puncture button 125 is pressed downward, a release member 125a pushes the holding portions 11b, 11c, and the engaging projections 122b, 122c are disengaged, allowing the pushing member 122 to be propelled forward by the biasing force of the coil spring 124, whereby the driving projection 122a of the pushing member 122 collides with the rear end of the needle body 21 of the puncture needle cartridge 20, as shown in FIG. 2. As a result, as shown in FIG. 7(b), the tip 212c of the puncturing portion 212a of the needle body 21 projects forward from the casing 22 to perform puncturing.

Figure 8:
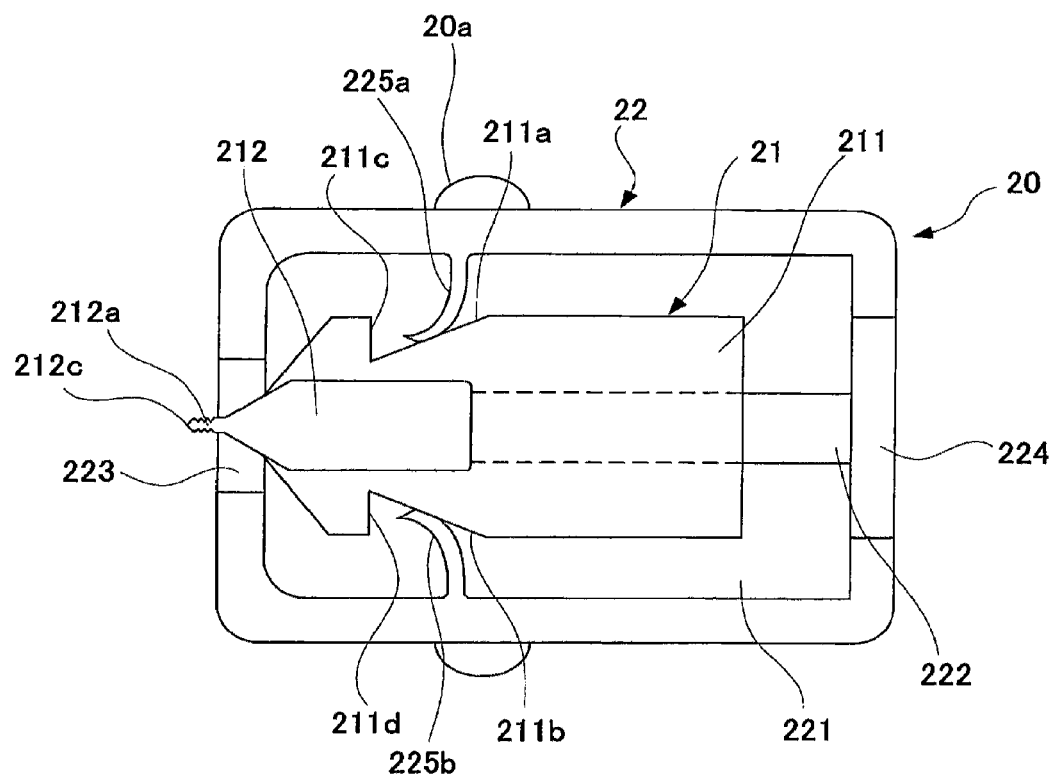
FIG. 8 is a cross-sectional view of the puncture needle cartridge during puncturing.

FIG. 8 is a cross-sectional view showing the interior of the puncture needle cartridge 20 during puncturing. The needle body 21 is held from laterally opposite sides by the flexible members 225a and 225b, and the guide projection 213 (see FIG. 3) is engaged with the guide groove 222, allowing the needle body to move precisely in the axial direction of the puncturing portion 212a. Accordingly, puncturing can be performed easily and reliably while preventing variation in the puncture direction due to differences in the collision direction and collision position of the driving projection 122a with the needle body 21. Furthermore, since the driving projection 122a of the plunger 12 and the needle body 21 are separated as described above, double puncturing due to vibration of the coil spring 124 after puncturing is prevented.

The engaging portions 211a, 211b are formed in the pedestal portion 211 in such a manner that the width of the pedestal portion 211 increases from the front towards the rear. Accordingly, with forward movement of the needle body 21, the deflection amount of the flexible members 225a, 225b that slide in contact with the engaging portions 211a, 211b gradually increases, allowing the elastic force for returning the deflection to gradually increase. FIG. 8 shows a state in which the tip 212c of the puncturing portion 212a projects outwardly from the casing 22 to the forwardmost position, i.e., a state in which the needle body 21 is in an extended position. From this state, the needle body 21 is retracted to a retracted position as shown in FIG. 2 by receiving a rearward biasing force upon release of the elastic force accumulated in the flexible members 225a, 225b. In the case that the steps 211c, 211d are formed on the front ends of engaging portions 211a, 211b as shown in this embodiment, rearward movement of the needle body 21 brings the steps 211c, 211d into contact with the front surface of the flexible members 225a, 225b so as to absorb the rearward biasing force, thus reliably retaining the needle body 21 in a retracted position.

After puncturing, the puncture needle cartridge 20 is detached from the mounting portion 11a of the puncturing device body 10, and a new puncture needle cartridge 20 is mounted to perform another puncturing.

As described above, according to the puncturing device 1 of this embodiment, the needle body 21 of the puncture needle cartridge 20 is held in a retracted position by the flexible members 225a and 225b before puncturing, and the needle body 21 is biased from an extended position to a retracted position after puncturing. Thus, the puncturing portion 212a can be reliably retained in the casing 22 before and after the puncturing. Accordingly, there is no necessity for the puncturing portion 212a to be covered with a cap etc., and improved workability and cost reduction can be realized by a simplified structure. Furthermore, the puncturing portion 212a is less visible to subjects, thus reducing their fear and anxiety.

If the pressing force applied to the needle body 21 is constant, there is a correlation between the inclination angle of the engaging portions 211a, 211b of the needle body 21, and the length of projection of the puncturing portion 212a. As the inclination angle becomes larger, the length of the projection becomes smaller. As the inclination angle becomes smaller, the length of the projection becomes larger. Accordingly, the length of projection of the puncturing portion 212a can be controlled by suitably adjusting the inclination angle. More specifically, as shown in FIG. 2, when the inclination angle of the engaging portion 211a is defined as $\theta$, $\tan \theta$ is preferably in the range of ½ to ⅓.

Furthermore, the inclined surface of the engaging portions 211a, 211b according to this embodiment is not necessarily planer (linear in plan view). The inclined surface may be a curved surface, such as a circular arc or elliptic arc surface, in plan view; or may be a combination of planar and curved surfaces. Further, the inclined surface may be stepped in plan view.

Figure 9:
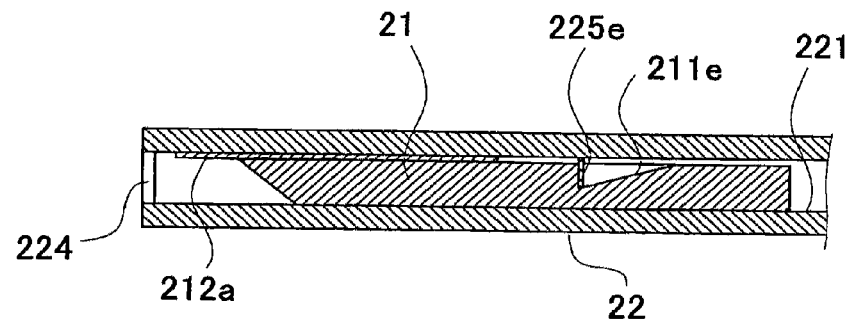
FIG. 9 is a partial cross-sectional view of another embodiment of the puncture needle cartridge of the present invention.

In the present invention, the guide groove 222 and the guide projection 213 are not always essential. The forward/backward movement of the needle body 21 can be guided by the flexible members 225a, 225b that hold the needle body 21 from laterally opposite sides. In this embodiment, the flexible members 225a, 225b are provided on laterally opposite sides of the needle body 21. However, it is also possible to form a flexible member only on one side of the needle body 21, and allow the opposite side of the needle body 21 to slide on the inner wall surface of the casing 22 to thereby guide the needle body 21 in a specific direction. For example, as shown in the cross-sectional view of FIG. 9, a part of the upper surface of the needle body 21 is recessed to form an engaging recessed portion 211e comprising an inclined surface, and the flexible member 225e that projects downward from the inside of the upper lid of the casing 22 is engaged with the engaging portion 211e, while the lower surface of the needle body 21 is allowed to slide on the bottom surface of the casing 22, to thereby control the right-left deflection and guide the forward/backward movement.

Figure 10:
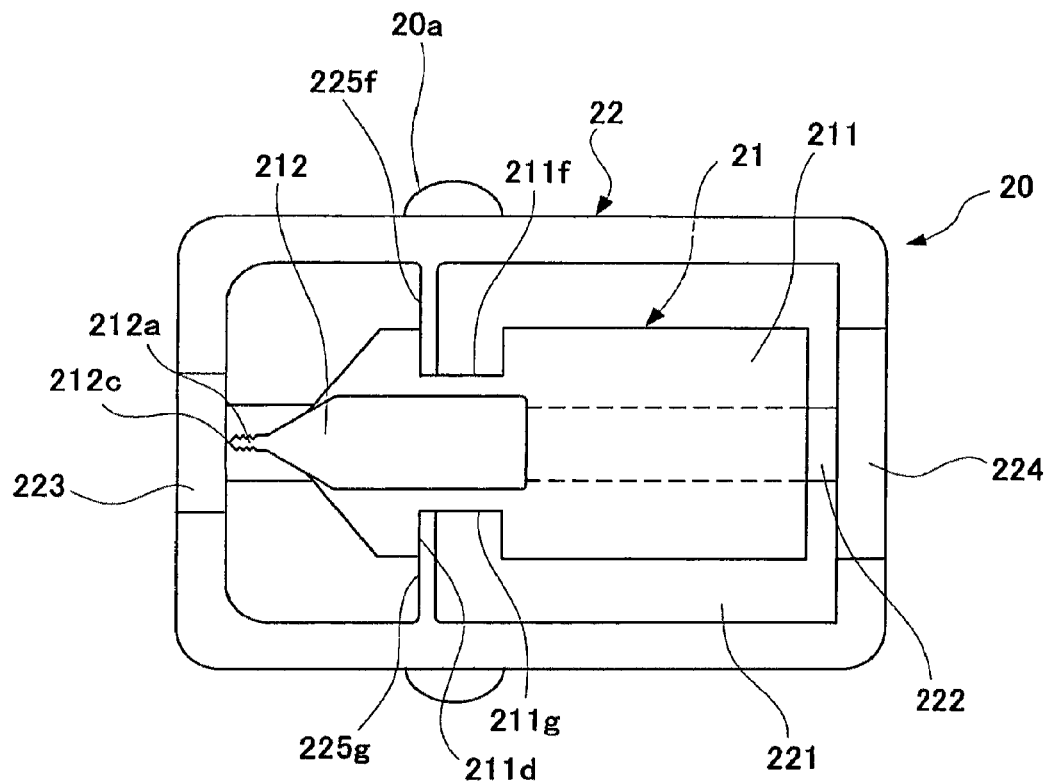
FIG. 10 is a cross-sectional view of another embodiment of the puncture needle cartridge of the present invention.

However, the inclined surface of the engaging portions to be engaged with the flexible members is not essential to provide the effect of the invention. For example, as shown in FIG. 10, slit grooves may be formed as engaging portions 211f, 211g on the right and left sides of the pedestal portion 211, and the tips of flexible members 225f, 225g may be housed in the engaging portions 211f, 211g. The flexible members 225f, 225g can be adapted to function as biasing means for biasing the needle body 21 in an extended position towards a retracted position.

Further, in this embodiment, the steps 211c, 211d formed at the tips of the engaging portions 211a, 211b ensure the return and retention of the needle body 21 to a retracted position. The steps 211c, 211d do not necessarily have a perpendicular surface with respect to the axis of the puncturing portion 212a. For example, as shown in FIG. 11, steps 211h, 211i each comprising an inclined surface angled to extend forwardly and outwardly may also be used.

Figure 11:
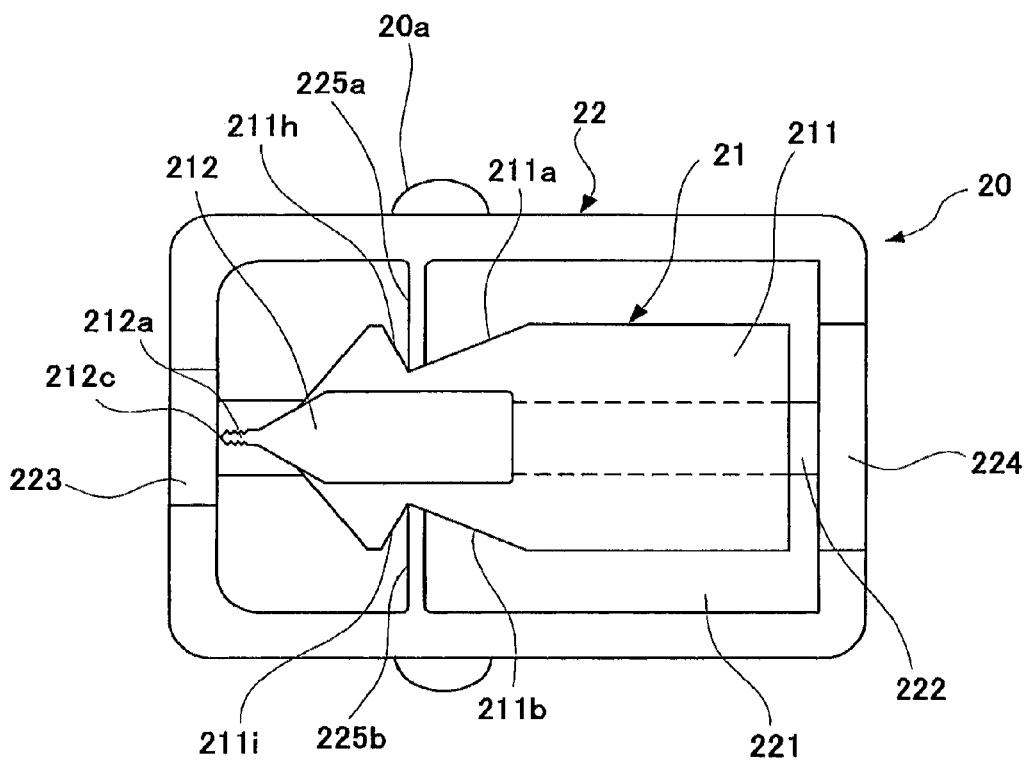
FIG. 11 is a cross-sectional view of another embodiment of the puncture needle cartridge of the present invention.

In the structure of FIG. 11, when the needle body 21 and the casing 22 are integrally molded, the needle body 21 and the casing 22 are connected only at the tips of the flexible members 225a, 225b after the molding, allowing the needle body 21 and the casing 22 to be easily separated from each other, and thus accomplishing a reduction in production cost.

Figure 12:
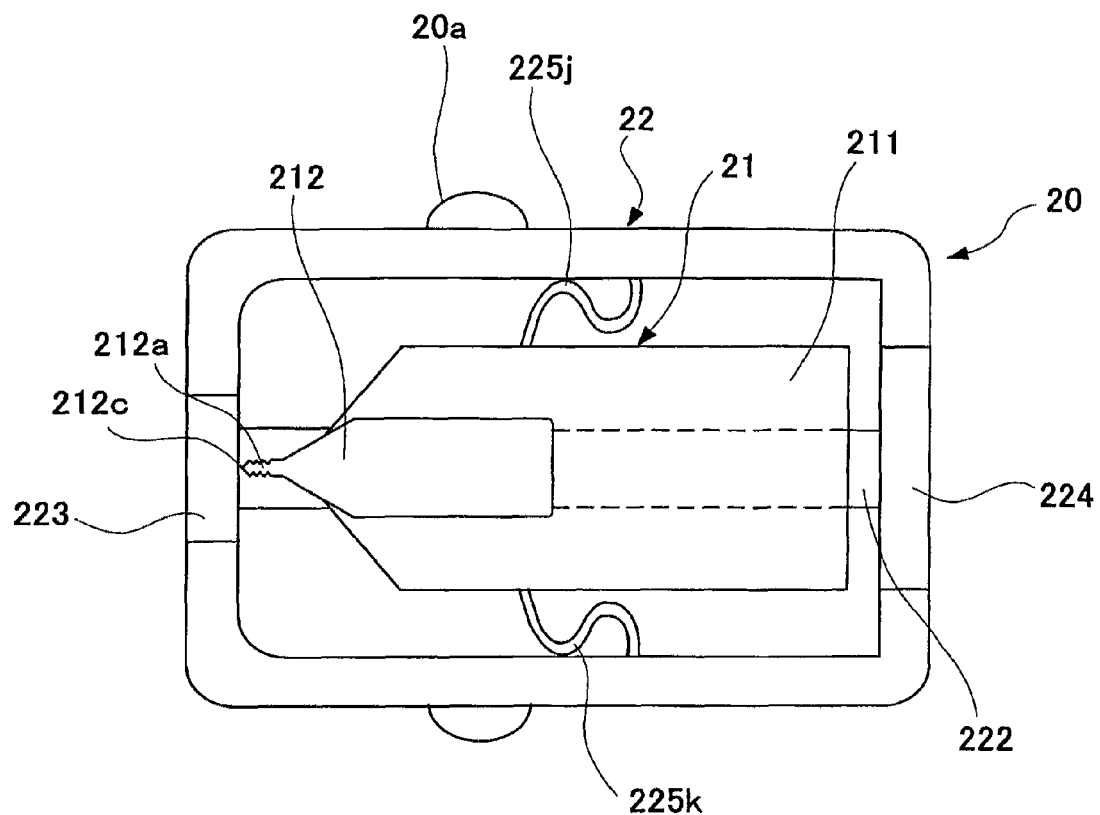
FIG. 12 is a cross-sectional view of another embodiment of the puncture needle cartridge of the present invention.

When the needle body 21 and the casing 22 are integrally molded, these parts do not necessarily have to be separated from each other, and can be used as is, i.e., in a state connected via the flexible members. For example, as shown in FIG. 12, the flexible members 225j, 211k may be curved and thus formed to be stretchable, and the needle body 21 and the casing 22 may be integrated via the flexible members 225j, 211k. The flexible members 225j, 211k may be disposed on laterally opposite sides of the needle body 21, as shown in FIG. 12. Alternatively, the flexible members 225j, 211k may be disposed on the rear side of the needle body 21 to increase biasing force towards a retracted position from an extended position.

In this embodiment, the engaging portions to be engaged with the flexible members are notches formed near the center of the pedestal portion 211. However, the positions of the engaging portions are not particularly limited. For example, the engaging portions may be inclined portions that are formed near the front end of the pedestal portion 211, and angled to taper towards the support portion 212.

Figure 13:
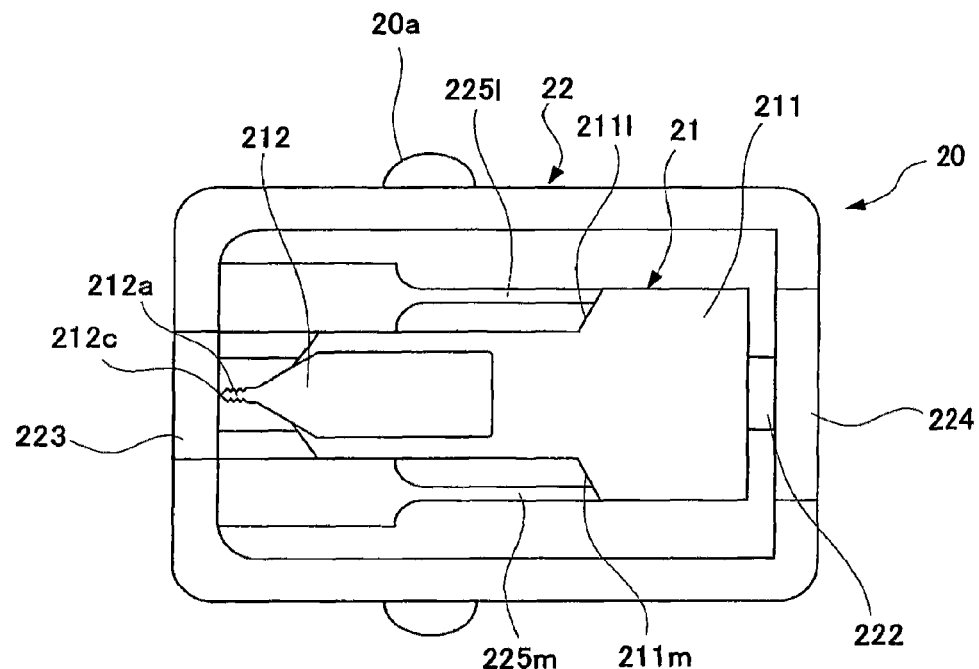
FIG. 13 shows cross-sectional views of another embodiment of the puncture needle cartridge of the present invention.
Figure 13:
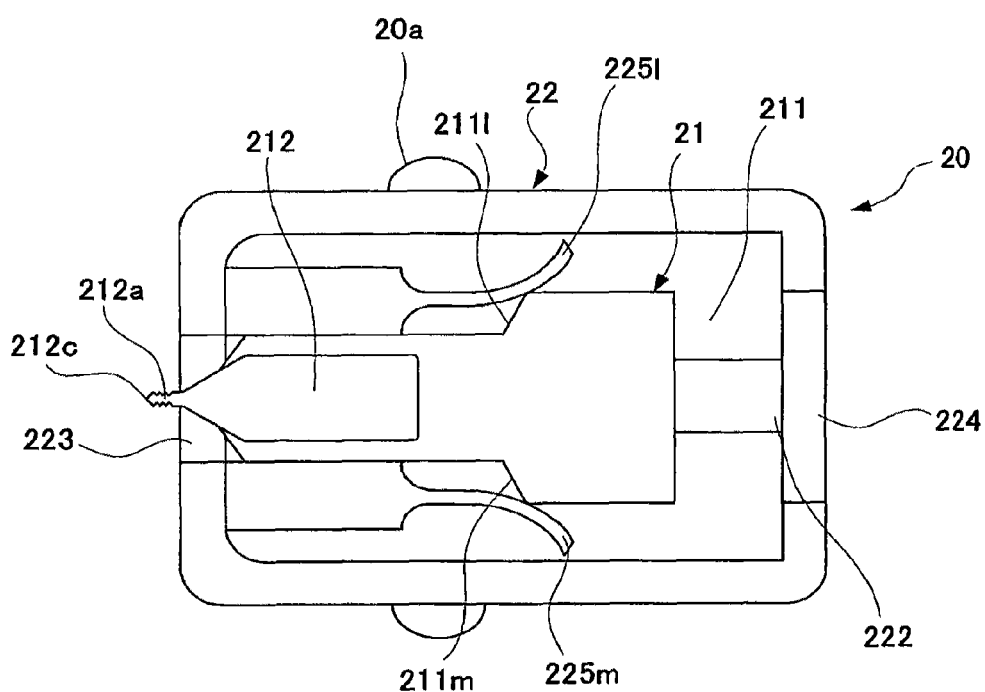
Figure 14:
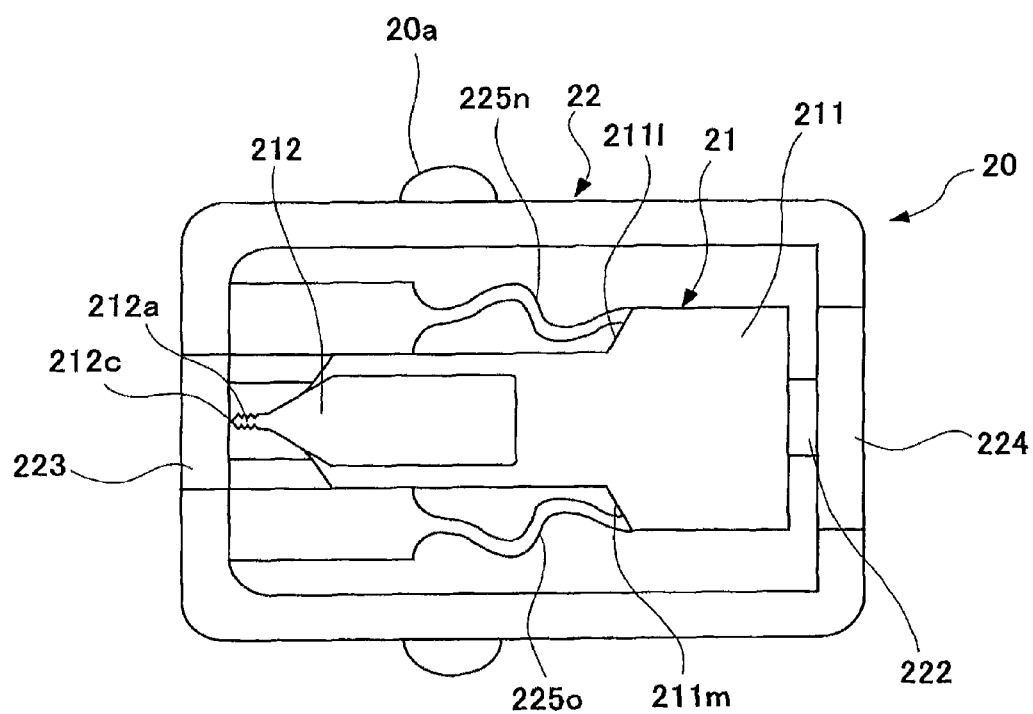
FIG. 14 is a cross-sectional view of another embodiment of the puncture needle cartridge of the present invention.

In this embodiment, the flexible members are formed along a plane perpendicular to the axis of the puncturing portion 212a. Alternatively, as shown in FIG. 13(a), flexible members 225l, 225m may be formed so as to extend in the same direction as the axis of the puncturing portion 212a, and tapered engaging portions 211l, 211m that project outwardly from laterally opposite sides of the needle body 21 may be engaged with the tips of the flexible members 225l, 225m. In this structure, when the needle body 21 moves forward to an extended position, the flexible members 225l, 225m are bent outward to hold the needle body 21 therebetween as shown FIG. 13(b), thus exerting biasing force towards a retracted position. In this case, the length of projection of the puncturing portion 212a and the biasing force can be adjusted by curving the flexible members 225n, 225o as shown in FIG. 14.

Figure 15:
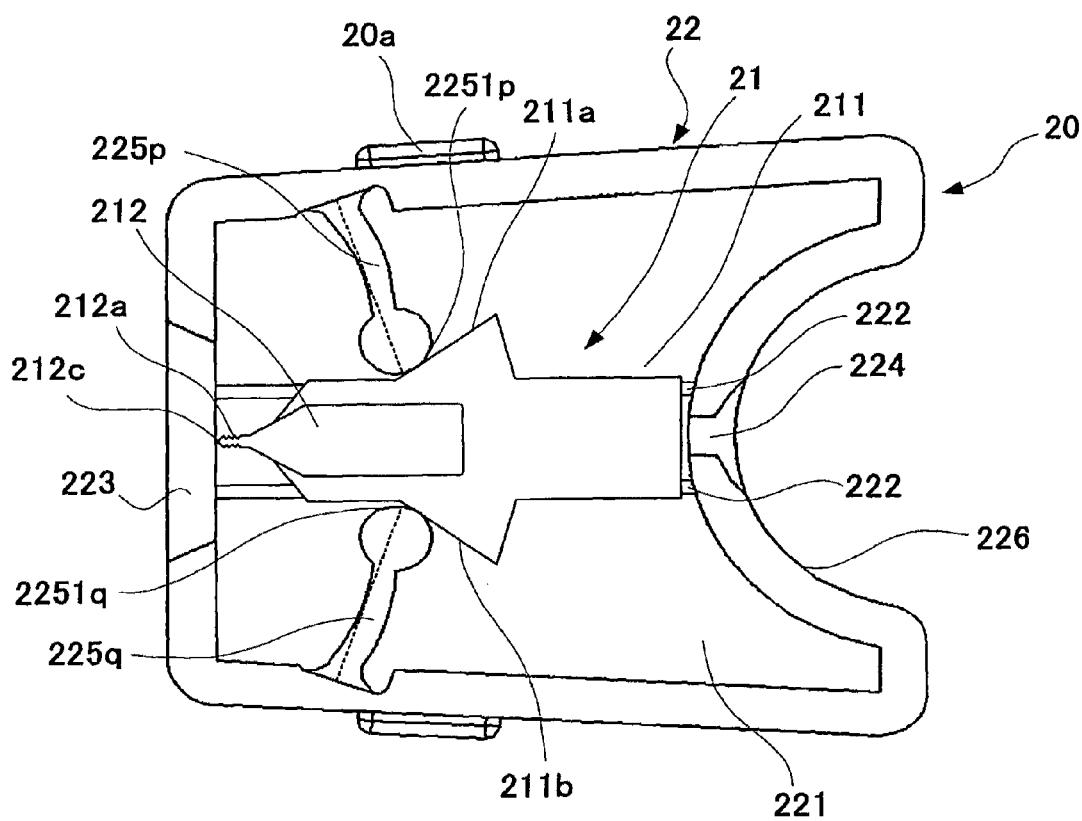
FIG. 15 is a cross-sectional view of another embodiment of the puncture needle cartridge of the present invention.

Alternatively, as shown in FIG. 15, circular arc abutment portions 2251p, 2251 may be formed at the tips of the flexible members 225p, 225q in the extension direction; and the abutment portions 2251p, 2251q may be brought into contact with the engaging portions 211a, 211b that are linear in plan view. According to this structure, when the needle body 21 moves, the needle body 21 and the flexible members 225p, 225q are brought into a substantially point-to-point contact in plan view, thus minimizing the contact area between the needle body 21 and the flexible members 225p, 225q, and enabling the needle body 21 to smoothly extend and retract. In this embodiment, the abutment portions 2251p, 2251q are disk-shaped. However, insofar as the portions brought into contact with the needle body 1 have a circular arc shape in plan view, the abutment portions may have, for example, a half-disk, spherical, or hemispherical shape.

As shown in FIG. 15, the flexible members 225p, 225q are curved to project backward, relative to the straight line (indicated by dashed lines in FIG. 15) connecting the centers of first and second ends of the flexible members 225p, 225q; the first end of which is fixed to the inner wall surface of the casing 22, and the second end of which has the abutment portions 2251p, 2251q. According to this structure, a sufficient level of biasing force can be easily applied to the needle body 21 in an extended position towards a retracted position, thus securely returning the needle body 21 to a retracted position.

Figure 16:
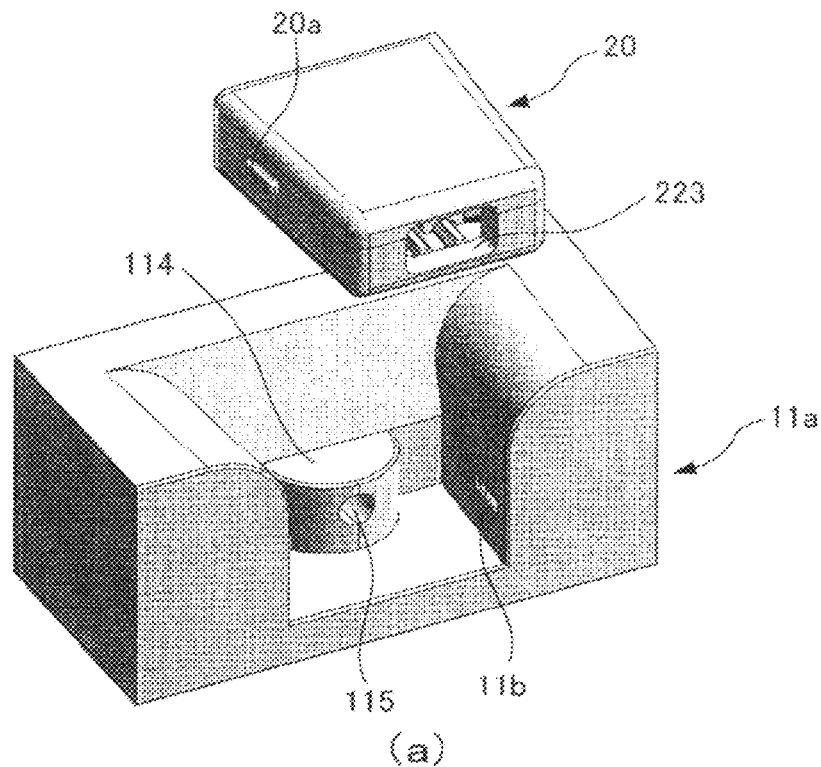
FIG. 16 shows perspective views of the puncture needle cartridge of FIG. 15 before the cartridge is mounted on a puncturing device body.
Figure 16:
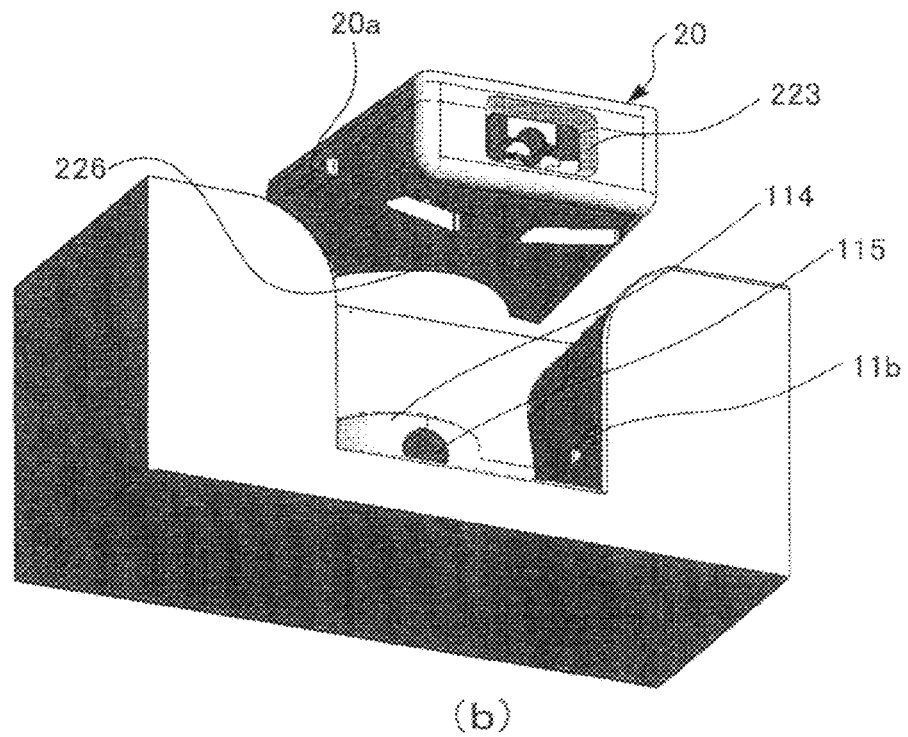
Figure 17:
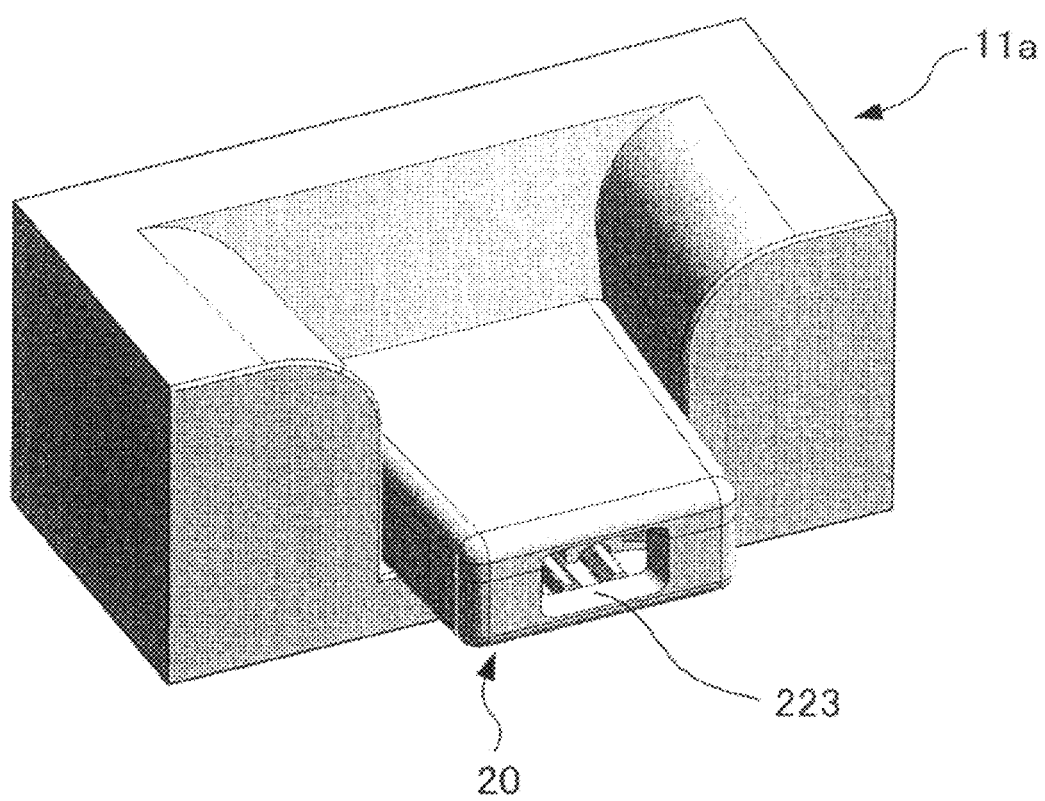
FIG. 17 is a perspective view of the puncture needle cartridge of FIG. 15 after the cartridge is mounted on a puncturing device body.

According to the puncture needle cartridge 20 shown in FIG. 15, both sides of the casing 22 are slightly tapered, and a semicircular recess 226 is formed on the rear surface of the casing 22. As shown in the perspective views of FIGS. 16(a) and (b) with the opening 223 for projecting the needle body being directed forward, the puncture needle cartridge 20 can be mounted on the mounting portion 11 from above in such a manner that the inner wall surface of the recess 226 slides along the side wall of the semi-cylindrical guide member 114 that is provided in the mounting portion 11a of the puncturing device body. As shown in FIG. 17, the rib 20a of the puncture needle cartridge 20 is engaged with the engaging recess 11b of the mounting portion 11a to thereby complete the mounting of the puncture needle cartridge 20 to the mounting portion 11a. The center of the guide member 114 has a through-hole 115 through which a rod-shaped pushing member (not shown) can extend straight forward, allowing the tip of the needle body of the puncture needle cartridge 20 to reliably project from the opening 223.

From the viewpoint of simplified structure and operational reliability, the biasing means for applying biasing force to the needle body of the puncture needle cartridge from an extended position towards a retracted position is preferably in the form of leaf springs, such as the various flexible members mentioned above. However, other various elastic members, such as coil springs, air springs, sponges, and rubbers, can also be used. Such elastic members are disposed on laterally opposite sides of the needle body 21, whereby the needle body 21 can be easily extended and retracted along the axis of puncturing portion 212a, allowing for easy and reliable puncturing. Alternatively, for example, a structure in which a micro-actuator, such as a micromotor utilizing piezoelectric elements, is driven to bias the needle body 21 via a guide wire, gear, or the like may be used as the biasing means.

The puncture needle cartridge 20 of the above embodiments can be preferably used for blood collection. However, the applications thereof are not particularly limited, and also include, for example, living tissue sampling and drug administration via the needle body 21.

According to the above embodiments, the puncture needle cartridge 20 is configured to be detachable from the puncturing device body 10. However, in the puncture needle cartridge 20 shown in FIG. 2, for example, if a pressing portion is provided on the rear side of the needle body 21 and the pressing portion is pressed forward, a puncturing device that can perform puncturing itself, without the need for a puncturing device body, can be provided.

Figure 18:
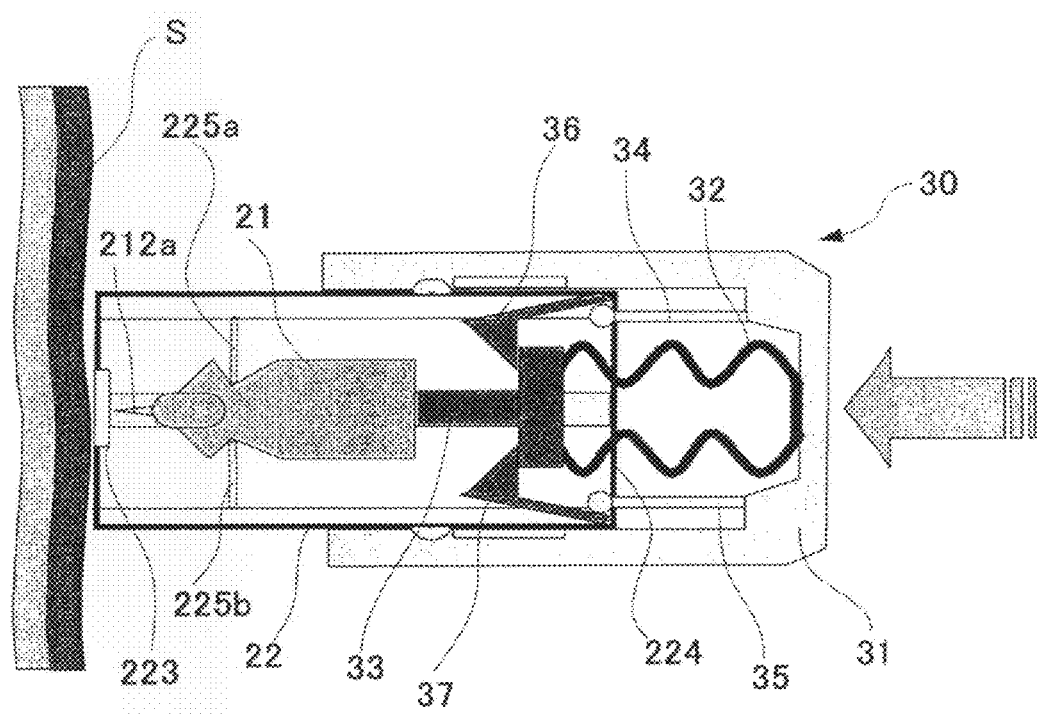
FIG. 18 is a cross-sectional view of the puncture needle cartridge.

FIG. 18 is a cross-sectional view of a puncturing device according to one embodiment of the present invention. The puncturing device 30 shown in FIG. 18 comprises the same major components as the puncture needle cartridge 20 shown in FIG. 2. The same reference symbols are assigned to the same components as those of FIG. 2; therefore, detailed explanations thereof will be omitted.

The puncturing device 30 comprises a cap 31 externally fitted on the rear end side of the casing 21. The inside of the top (rear portion) of the cap 31 has a plunger 33 connected thereto via a bellows-like spring 32, and release projections 34, disposed on laterally opposite sides of the spring 32. The spring 32 extends into the casing 22 through the rear opening 22. The plunger 33 is disposed in the casing 22 in such a manner that the front end of the plunger 33 abuts against the rear surface of the needle body 21.

A pair of plunger receiving members 36, 37 is provided on laterally opposite sides of the plunger 33 in the casing 22. The plunger receiving members 36, 37 comprise flexible members; the base side of the plunger receiving members is fixed to the inner surface of the rear portion of the casing 22, and the front ends of the plunger receiving members are engaged with the flange of the plunger 33 so as to lock the forward movement of the plunger 33.

The puncturing device 30 with the above configuration is such that when the cap 31 is pushed in the arrow direction with the front end of the casing 22 being pressed against the skin S, the cap 31 moves forward and the spring 32 disposed between the cap 31 and the plunger 33 shrinks to accumulate biasing force. When the cap 31 is further pushed, the tips of the release projections 34, 35 are brought into contact with the plunger receiving members 36, 37 to push the plunger receiving members outward, thus unlocking the plunger 33. As a result, the plunger 33 is vigorously extended by the biasing force of the spring 32, and collides with the needle body 21 to puncture the skin S. After puncturing, the needle body 21 retracts from an extended position to a retracted position due to the biasing force of flexible members 225a, 225b, as with the puncture needle cartridge 20 shown in FIG. 2.

The puncturing device of this embodiment is configured in such a manner that the needle body 21 can be pressed through the rear opening 224 of the casing 22, and the direction and depth of puncturing by the needle body 21 can be precisely controlled. Therefore, it can be preferably used as a safety lancet, and can also be used as a device for various medical purposes, such as living tissue sampling and vaccination.

DESCRIPTION OF THE REFERENCE NUMERALS

1: puncturing device
10: puncturing device body
12: plunger
20: puncture needle cartridge
21: needle body
211a, 211b: engaging portions 211c and 211d: steps
212a: puncturing portion
212c: tip
22: casing
223, 224: openings
225a, 225b: flexible members

The invention claimed is:

1. A puncture needle cartridge for detachably mounting on a puncturing device body to form a puncturing device, the puncture needle cartridge comprising:
   a needle body having a puncturing portion and a pair of engaging portions, each of the engaging portions having a tapered inclined surface;
   a casing for housing the needle body, the casing having a pair of flexible members, and the casing having openings that are respectively formed in front of and behind the needle body;
   the needle body being mounted to be movable between a retracted position, wherein a tip of the puncturing portion is retracted in the casing, and an extended position, wherein the tip of the puncturing portion is projected outward from the casing, by receiving a pressing force from the puncturing device body,
   wherein the pair of flexible members are on opposite sides of the needle body to bias the needle body from the extended position towards the retracted position, a first end of each flexible member being fixed to an inner surface of the casing, and a second end of each flexible member being configured to slide in contact with a corresponding engaging portion,
   wherein a circular arc shaped abutment portion formed at a tip of each flexible member contacts a corresponding engaging portion from among the pair of engaging portions, the corresponding engaging portion being linear in plan view,
   wherein the second end of each flexible member is engaged with the needle body, and
   wherein each flexible member is curved to project backward.

2. The puncture needle cartridge according to claim 1, wherein the pair of flexible members are on laterally opposite sides of the needle body.

3. The puncture needle cartridge according to claim 1, wherein the needle body and the casing are integrally molded using a biocompatible material.

4. A puncture needle cartridge for detachably mounting on a puncturing device body to form a puncturing device, the puncture needle cartridge comprising:
   a needle body having a puncturing portion and a pair of engaging portions, each of the engaging portions having a tapered inclined surface;
   a casing for housing the needle body, the casing having a pair of flexible members, and the casing having openings that are respectively formed in front of and behind the needle body;
   the needle body being mounted to be movable between a retracted position, wherein a tip of the puncturing portion is retracted in the casing, and an extended position, wherein the tip of the puncturing portion is projected outward from the casing, by receiving a pressing force from the puncturing device body,
   wherein the pair of flexible members are on opposite sides of the needle body to bias the needle body from the extended position towards the retracted position, a first end of each flexible member being fixed to an inner surface of the casing, and a second end of each flexible member being configured to slide in contact with a corresponding engaging portion,
   wherein a circular arc shaped abutment portion formed at a tip of each flexible member contacts a corresponding engaging portion from among the pair of engaging portions, the corresponding engaging portion being linear in plan view, and wherein the flexible members are curved to project backward relative to a straight line connecting centers of first and second ends of the flexible members, the first end of which is fixed to the inner wall surface of the casing, and the second end of which includes the circular arc shaped abutment portions.

5. The puncture needle cartridge according to claim 4, wherein the pair of flexible members are on laterally opposite sides of the needle body.

6. The puncture needle cartridge according to claim 4, wherein the second end of each flexible member is engaged with the needle body.

7. The puncture needle cartridge according to claim 4, wherein the needle body and the casing are integrally molded using a biocompatible material.

8. The puncture needle cartridge according to claim 4, wherein a curvature between the first and second ends of the flexible members has a concave surface facing the puncturing portion of the needle body.

9. A puncture needle cartridge for detachably mounting on a puncturing device body to form a puncturing device, the puncture needle cartridge comprising:
   a needle body having a puncturing portion and a pair of engaging portions, each of the engaging portions having a tapered inclined surface;
   a casing for housing the needle body, the casing having a pair of flexible members, and the casing having openings that are respectively formed in front of and behind the needle body;
   the needle body being mounted to be movable between a retracted position, wherein a tip of the puncturing portion is retracted in the casing, and an extended position, wherein the tip of the puncturing portion is projected outward from the casing, by receiving a pressing force from the puncturing device body,
   wherein the pair of flexible members are on opposite sides of the needle body to bias the needle body from the extended position towards the retracted position, a first end of each flexible member being fixed to an inner surface of the casing, and a second end of each flexible member being configured to slide in contact with a corresponding engaging portion,
   wherein a circular arc shaped abutment portion formed at a tip of each flexible member contacts a corresponding engaging portion from among the pair of engaging portions, the corresponding engaging portion being linear in plan view, and
   wherein the flexible members have a concave curvature between the first and second ends of the flexible members, the first end of which is fixed to the inner wall surface of the casing, and the second end of which includes the circular arc shaped abutment portion.

10. The puncture needle cartridge according to claim 9, wherein the curvature between the first and second ends of the flexible members has a concave surface facing the puncturing portion of the needle body.

11. The puncture needle cartridge according to claim 9, wherein the pair of flexible members are on laterally opposite sides of the needle body.

12. The puncture needle cartridge according to claim 9, wherein the second end of each flexible member is engaged with the needle body.

13. The puncture needle cartridge according to claim 9, wherein the needle body and the casing are integrally molded using a biocompatible material.

14. The puncture needle cartridge according to claim 9, wherein a curvature between the first and second ends of the flexible members has a concave surface facing the puncturing portion of the needle body.

15. The puncture needle cartridge according to claim 9, wherein each flexible member is curved to project backward.

* * * * *